(12) United States Patent
Thorne, IV et al.

(10) Patent No.: US 10,648,023 B2
(45) Date of Patent: May 12, 2020

(54) SYSTEMS AND METHODS FOR SAMPLING OF AMPLIFICATION PRODUCTS

(71) Applicant: CALIPER LIFE SCIENCES, INC., Hopkinton, MA (US)

(72) Inventors: Edward H. Thorne, IV, North Grafton, MA (US); Abbie L. Esterman, Northboro, MA (US)

(73) Assignee: CALIPER LIFE SCIENCES, INC., Hopkinton, MA (US)

( * ) Notice: Subject to any disclaimer, the term of this patent is extended or adjusted under 35 U.S.C. 154(b) by 346 days.

(21) Appl. No.: 15/634,622

(22) Filed: Jun. 27, 2017

(65) Prior Publication Data

US 2017/0292152 A1 Oct. 12, 2017

Related U.S. Application Data

(62) Division of application No. 13/689,537, filed on Nov. 29, 2012, now Pat. No. 9,689,029.

(Continued)

(51) Int. Cl.
*G01N 1/10* (2006.01)
*C12Q 1/6851* (2018.01)
(Continued)

(52) U.S. Cl.
CPC ...... *C12Q 1/6851* (2013.01); *B01L 3/502715* (2013.01); *B01L 7/52* (2013.01);
(Continued)

(58) Field of Classification Search
CPC ................ G01N 27/447; B01J 19/0046; B01J 2219/00608
(Continued)

(56) References Cited

U.S. PATENT DOCUMENTS 4,683,195 A 7/1987 Mullis et al.
4,683,202 A 7/1987 Mullis
(Continued)

FOREIGN PATENT DOCUMENTS

| WO | WO 2002063288 A1 | 8/2002 |
| WO | WO 2011/036289 A1 | 3/2011 |
| WO | WO 2011090396 A1 | 7/2011 |

OTHER PUBLICATIONS

EPO Examination Report, issued in corresponding application No. EP 12 798 563.8, dated Jan. 21, 2019.
(Continued)

*Primary Examiner* — Natalia Levkovich
(74) *Attorney, Agent, or Firm* — Day Pitney LLP

(57) ABSTRACT

The invention provides systems and methods for processing samples. In a method, a reaction card is provided that has a channel network, a valve, and a micropump, all disposed within the card. The reaction card also has a collection well disposed on a surface of the card and a tubular member extending out from the card. A reaction vessel is provided and affixed to the reaction card such that the tubular member is inserted into the reaction vessel. Amplification reaction reagents and a sample are delivered into the reaction vessel, and an amplification reaction is initiated within the reaction vessel, resulting in an amplification product being disposed within the reaction vessel. The valve is opened to atmosphere, and the first micropump is activated to pump an aliquot of reaction product from the reaction vessel into the tubular member, through the channel network, and into the collection well.

12 Claims, 3 Drawing Sheets

Related U.S. Application Data

(60) Provisional application No. 61/566,151, filed on Dec. 2, 2011.

(51) Int. Cl.
    *B01L 3/00*     (2006.01)
    *B01L 7/00*     (2006.01)

(52) U.S. Cl.
    CPC ..... *B01L 2200/027* (2013.01); *B01L 2200/10* (2013.01); *B01L 2300/044* (2013.01); *B01L 2300/0816* (2013.01); *B01L 2300/0832* (2013.01); *B01L 2300/0867* (2013.01); *B01L 2400/0421* (2013.01); *B01L 2400/0487* (2013.01); *B01L 2400/0683* (2013.01)

(58) Field of Classification Search
    USPC .......................................... 436/180; 422/554
    See application file for complete search history.

(56) References Cited

U.S. PATENT DOCUMENTS

| | | | |
|---|---|---|---|
| 4,800,159 | A | 1/1989 | Mullis et al. |
| 5,639,428 | A | 6/1997 | Cottingham |
| 5,939,291 | A | 8/1999 | Loewy et al. |
| 5,955,029 | A | 9/1999 | Wilding et al. |
| 5,965,410 | A | 10/1999 | Chow et al. |
| 6,124,138 | A | 9/2000 | Woudenberg et al. |
| 6,171,850 | B1 | 1/2001 | Nagle et al. |
| 6,303,029 | B1 | 10/2001 | Nurok et al. |
| 6,303,305 | B1 | 10/2001 | Wittwer et al. |
| 6,303,343 | B1 | 10/2001 | Kopf-Sill |
| 6,306,590 | B1 | 10/2001 | Mehta et al. |
| 6,391,622 | B1 | 5/2002 | Knapp et al. |
| 6,406,893 | B1 | 6/2002 | Knapp et al. |
| 6,444,461 | B1 | 9/2002 | Knapp et al. |
| 6,984,516 | B2 | 1/2006 | Briscoe et al. |
| 2003/0148922 | A1 | 8/2003 | Knapp et al. |
| 2003/0152994 | A1 | 8/2003 | Woudenberg et al. |
| 2006/0062696 | A1* | 3/2006 | Chow ............... B01L 3/502746 422/400 |
| 2007/0134652 | A1 | 6/2007 | Slepnev et al. |
| 2009/0186344 | A1 | 7/2009 | Farinas |
| 2010/0047774 | A1 | 2/2010 | Van Haag et al. |
| 2010/0120129 | A1 | 5/2010 | Amshey et al. |
| 2010/0261159 | A1 | 10/2010 | Hess et al. |
| 2010/0294811 | A1 | 11/2010 | Akechi et al. |
| 2011/0312622 | A1 | 12/2011 | Azimi et al. |

OTHER PUBLICATIONS

Grover et al., "Monolithic membrane valves and diaphragm pumps for practical large-scale integration into glass microfluidic devices," Sensors and Actuators B: Chemical: International Journal Devoted to Research and Development of Physical and Chemical Transducers, Elsevier BV, NL, vol. 89, No. 3 (Apr. 1, 2003) pp. 315-323.

Liu et al., "Integrated DNA purification, PCR, sample cleanup, and capillary electrophoresis microchip for forensic human identification," Lab on a Chip, vol. 11, No. 6 (Jan. 1, 2011), p. 1041.

USPTO Non-Final Office Action with Notice of References Cited by Examiner, issued in corresponding U.S. Appl. No. 13/689,537, dated Apr. 22, 2015.

USPTO Final Office Action with Notice of References cited by Examiner, issued in corresponding U.S. Appl.l No. 13/689,537, dated Jan. 11, 2016.

USPTO Non-Final Office Action, issued in corresponding U.S. Appl. No. 13/689,537, dated Oct. 21, 2016.

EPO Examination Report, issued in corresponding application No. Ep 12 798 563.8, dated Jul. 9, 2018.

International Search Report, issued in corresponding international application No. PCT/US12/67122, dated Mar. 8, 2013.

International Preliminary Report on Patentability and Written Opinion of the International Searching Authority, issued in corresponding international application No. PCT/US12/67122, dated Mar. 8, 2013.

Guolin Xu et al, "A self-contained all-in-one cartridge for sample preparation and real-time PCR in rapid influenza diagnosis", Lab on a Chip, The Royal Society of Chemistry, (2010) vol. 10, No. 22, pp. 3103-3111.

Kopp et al., "Chemical Amplification: Continuous-Flow PCR on a Chip" Science, 280 (May 15, 1998), pp. 1046-1048.

Pal, R. et al., "An integrated microfluidic device for influenza and other genetic analyses", Lab on a Chip, The Royal Society of Chemistry 2005, vol. 5, (Aug. 18, 2005), pp. 1024-1032.

Zhang et al., "PCR microfluidic devices for DNA amplification", Biotechnology Advances 2006, vol. 24, available on-line, (Dec. 2, 2005), pp. 243-284.

\* cited by examiner

SYSTEMS AND METHODS FOR SAMPLING OF AMPLIFICATION PRODUCTS

CROSS REFERENCE TO RELATED APPLICATION

This application is a divisional application of and claims the benefit of U.S. patent application Ser. No. 13/689,537, filed Nov. 29, 2012, which claims the benefit of U.S. Provisional Application No. 61/566,151, filed Dec. 2, 2011, all of which are incorporated herein by reference in their entirety for all purposes.

TECHNICAL FIELD

The present disclosure is in the field of nucleic acid detection. In particular, herein are systems and methods for sampling of amplification products during an amplification reaction and for analyzing the sampled products.

BACKGROUND OF THE INVENTION

Detection of nucleic acids is central to gene expression analysis, diagnostics, medicine, forensics, industrial processing, crop and animal breeding, and many other fields. For example, nucleic acid detection technology is used to diagnose disease conditions, detect infectious organisms, determine genetic lineage and genetic markers, correctly identify individuals at crime scenes, and propagate industrial organisms.

The introduction of nucleic acid amplification methods has greatly improved the specificity and sensitivity of nucleic acid detection. One of the most commonly used methods of nucleic acid amplification is polymerase chain reaction (PCR), which amplifies nucleic acids by using sequence specific primers targeted to opposing strands of double stranded DNA to copy a desired DNA sequence. Multiple cycles of primer annealing, DNA polymerization and double-stranded DNA denaturation are used to exponentially amplify a desired segment of DNA. Reactions with only one copy of template DNA can be rapidly and specifically amplified more than 100 million fold (see, e.g., U.S. Pat. Nos. 4,683,195, 4,683,202 and 4,800,159).

Other methods for amplification of nucleic acids include reverse-transcriptase PCR (RT-PCR), nucleic acid sequence-based amplification (NASBA), transcription-based amplification system (TAS), self-sustained sequence replication (3SR), ligation amplification reaction (LAR), Q-beta amplification, and ligase chain reaction (LCR). Many of these amplification reactions utilize a polymerase enzyme or fragment thereof.

Details regarding the use of these and other amplification methods can be found in any of a variety of standard texts, including, e.g., Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2002) ("Ausubel") and PCR Protocols A Guide to Methods and Applications (Innis et al. eds) Academic Press Inc. San Diego, Calif. (1990) (Innis). Many available biology texts have extended discussions regarding PCR and related amplification methods.

Analytical sensitivity is an important consideration when conducting quantitative PCR. Many methods exist for detecting amplified nucleic acid products. Some methods (see, e.g., U.S. Pat. No. 4,683,195) utilize dot-blots, oligonucleotide arrays, size-separation by gel electrophoresis, Sanger sequencing, and various hybridization probes, and may require post-reaction processing.

A number of miniaturized approaches to performing PCR and other amplification reactions have been developed, e.g., involving amplification reactions in microfluidic devices, as well as methods for detecting and analyzing amplified nucleic acids in or on the devices. Details regarding such technology can be found in the technical and patent literature (e.g., U.S. Pat. No. 6,444,461 to Knapp, et al. (Sep. 3, 2002) MICROFLUIDIC DEVICES AND METHODS FOR SEPARATION; U.S. Pat. No. 6,406,893 to Knapp, et al. (Jun. 18, 2002) MICROFLUIDIC METHODS FOR NON-THERMAL NUCLEIC ACID MANIPULATIONS; U.S. Pat. No. 6,391,622 to Knapp, et al. (May 21, 2002) CLOSED-LOOP BIOCHEMICAL ANALYZERS; U.S. Pat. No. 6,306,590 to Mehta, et al. (Oct. 23, 2001) Microfluidic matrix localization apparatus and methods; U.S. Pat. No. 6,303,343 to Kopf-Sill (Oct. 16, 2001) INEFFICIENT FAST PCR; U.S. Pat. No. 6,171,850 to Nagle, et al. (Jan. 9, 2001) INTEGRATED DEVICES AND SYSTEMS FOR PERFORMING TEMPERATURE CONTROLLED REACTIONS AND ANALYSES; U.S. Pat. No. 5,939,291 to Loewy, et al. (Aug. 17, 1999) MICROFLUIDIC METHOD FOR NUCLEIC ACID AMPLIFICATION; U.S. Pat. No. 5,955,029 to Wilding, et al. (Sep. 21, 1999) MESOSCALE POLYNUCLEOTIDE AMPLIFICATION DEVICE AND METHOD; U.S. Pat. No. 5,965,410 to Chow, et al. (Oct. 12, 1999) ELECTRICAL CURRENT FOR CONTROLLING FLUID PARAMETERS IN MICROCHANNELS, and many others).

Despite the widespread use of amplification technologies and the adaptation of these technologies to miniaturized systems, certain technical difficulties persist in amplifying and detecting nucleic acids. Nucleic acid amplification methods, because of their ability to greatly amplify template nucleic acids, are prone to false positive results due to sample contamination, particularly contamination due to sample carryover. Some methods also require substantial sampling volume.

Thus, there remains a need for improved systems and methods for detecting and quantifying nucleic acids with increased sensitivity while minimizing contamination and sampling volume.

SUMMARY OF THE INVENTION

One aspect of the present invention is a system for processing samples. The system comprises a reaction card and a reaction vessel assembly. The reaction card comprises a channel network, a valve, and a micropump, all of which are disposed within the card. The reaction card further comprises a collection well disposed on a surface of the card and a first tubular member extending out from the card. The valve and the micropump are operably connected with the channel network, and the collection well and the first tubular member are in fluid communication with the channel network. The reaction vessel assembly comprises a reaction vessel. The reaction vessel assembly is affixed to the reaction card such that the first tubular member is inserted into the reaction vessel.

Another aspect of the present invention is a method for processing samples. In the method, a reaction card is provided, the reaction card comprising a channel network, a valve, and a first micropump, all of which are disposed within the card. The reaction card further comprises a collection well disposed on a surface of the card and a first tubular member extending out from the card. A reaction vessel is provided and affixed to the reaction card such that the tubular member is inserted into the reaction vessel. Amplification reaction reagents and a sample are delivered into the reaction vessel, and an amplification reaction is initiated within the reaction vessel, resulting in an amplification product being disposed within the reaction vessel. The valve is opened to atmosphere, and the first micropump is activated to pump a first aliquot of reaction product from the reaction vessel into the tubular member, through the channel network, and into the collection well.

The aforementioned and other features and advantages of the invention will become further apparent from the following detailed description of the presently preferred embodiments, read in conjunction with the accompanying drawings, which are not to scale. In the drawings, like reference numbers indicate identical or functionally similar elements. The detailed description and drawings are merely illustrative of the invention, rather than limiting, the scope of the invention being defined by the appended claims and equivalents thereof.

DETAILED DESCRIPTION OF THE PRESENTLY PREFERRED EMBODIMENTS

Figure 4:
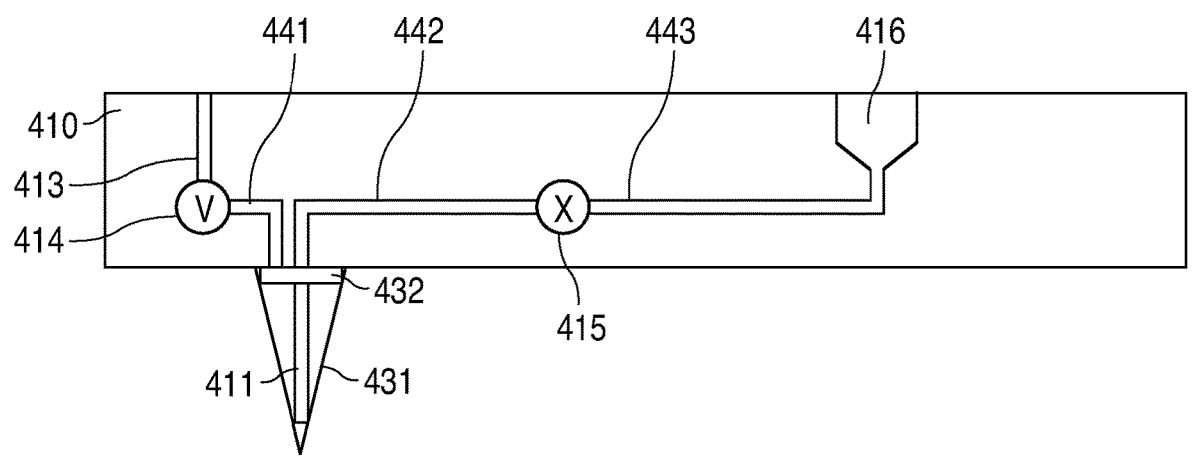
FIG. 4 is a side, cutaway view of a system for processing samples, in accordance with the present invention.
Figure 5:
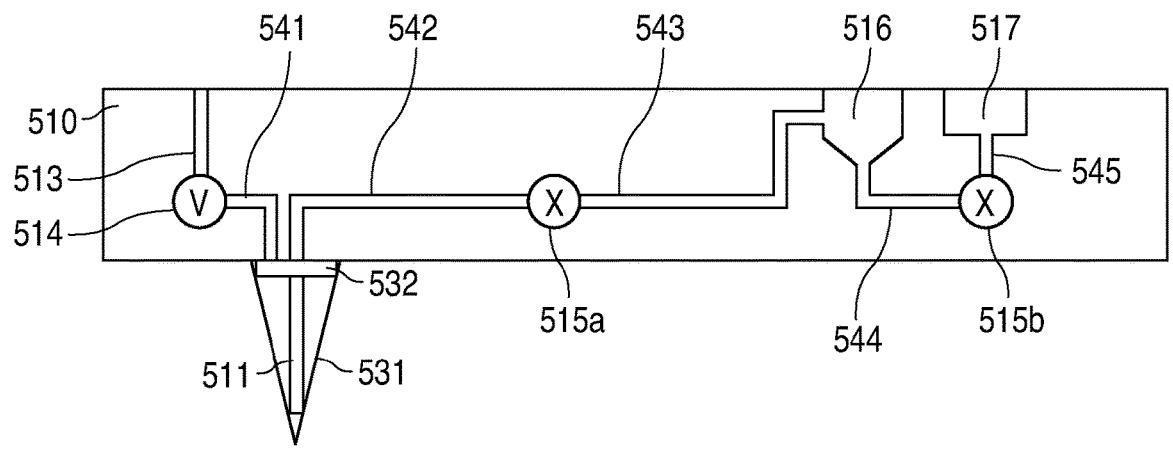
FIG. 5 is a side, cutaway view of another system for processing samples, in accordance with the present invention.
Figure 6:
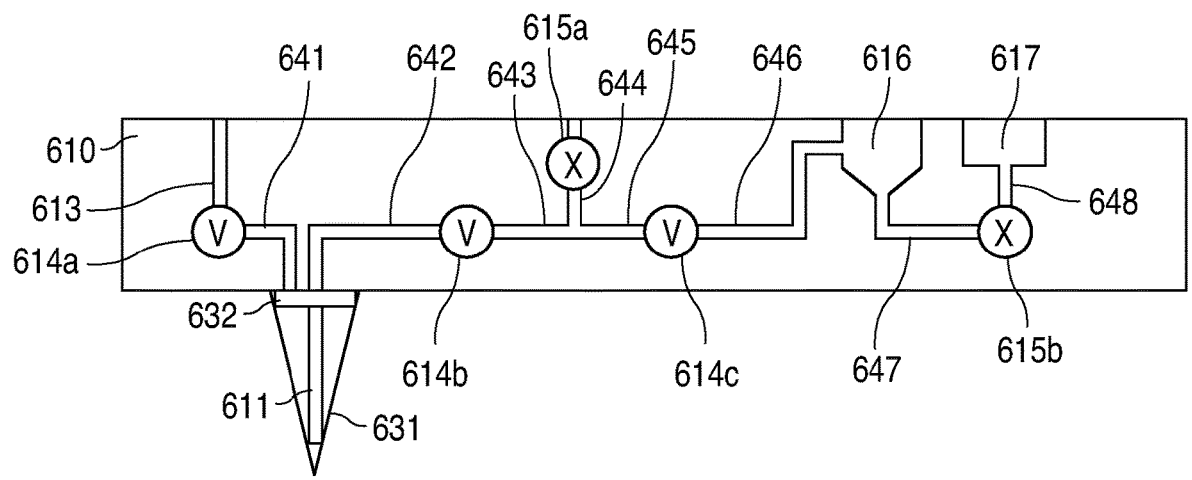
FIG. 6 is a side, cutaway view of yet another system for processing samples, in accordance with the present invention.

One aspect of the present invention is a system for processing samples. The system comprises a reaction card and a reaction vessel assembly, seen at 110 and 130, respectively, in FIG. 1. The system may further comprise a reagent tube assembly, seen at 120 in FIG. 1. Additional embodiments of the reaction card are illustrated at 410 in FIG. 4, 510 in FIG. 5, and 610 in FIG. 6. FIGS. 4-6 illustrate reaction cards having a single channel network, but each reaction card may incorporate an array of channel networks, with one channel network being provided for each reaction vessel affixed to the reaction card.

Figure 1:
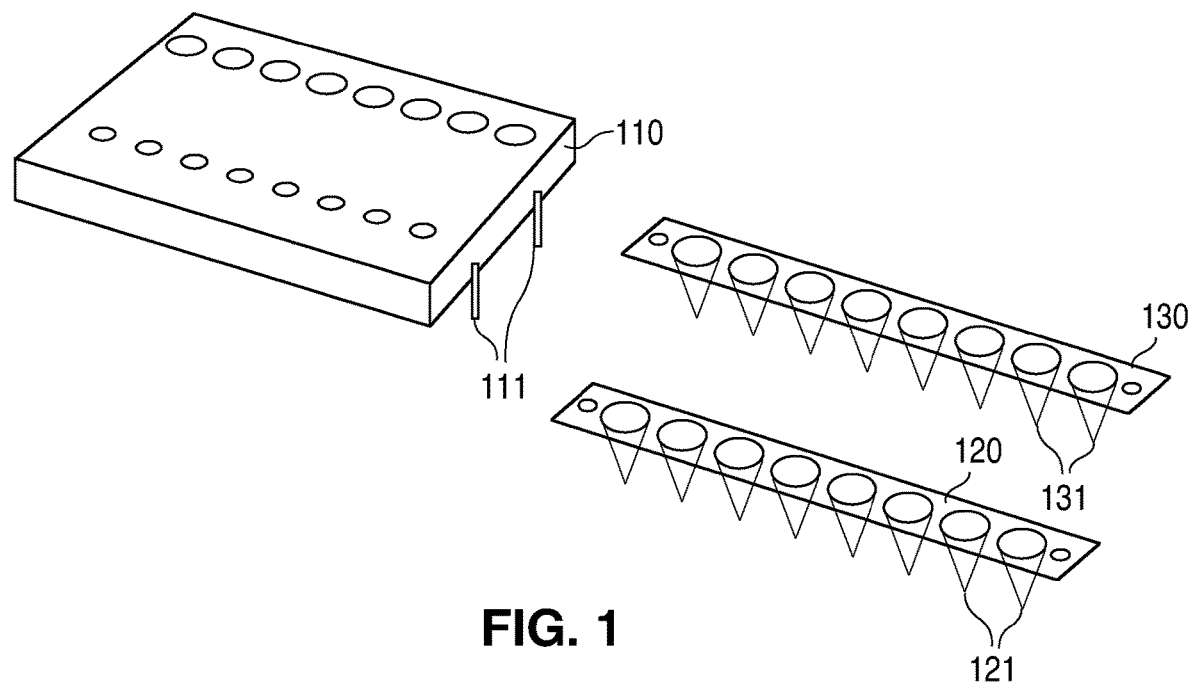
FIG. 1 is a perspective view of a reaction card, a reagent tube assembly, and a reaction vessel assembly, in accordance with the present invention.
Figure 3:
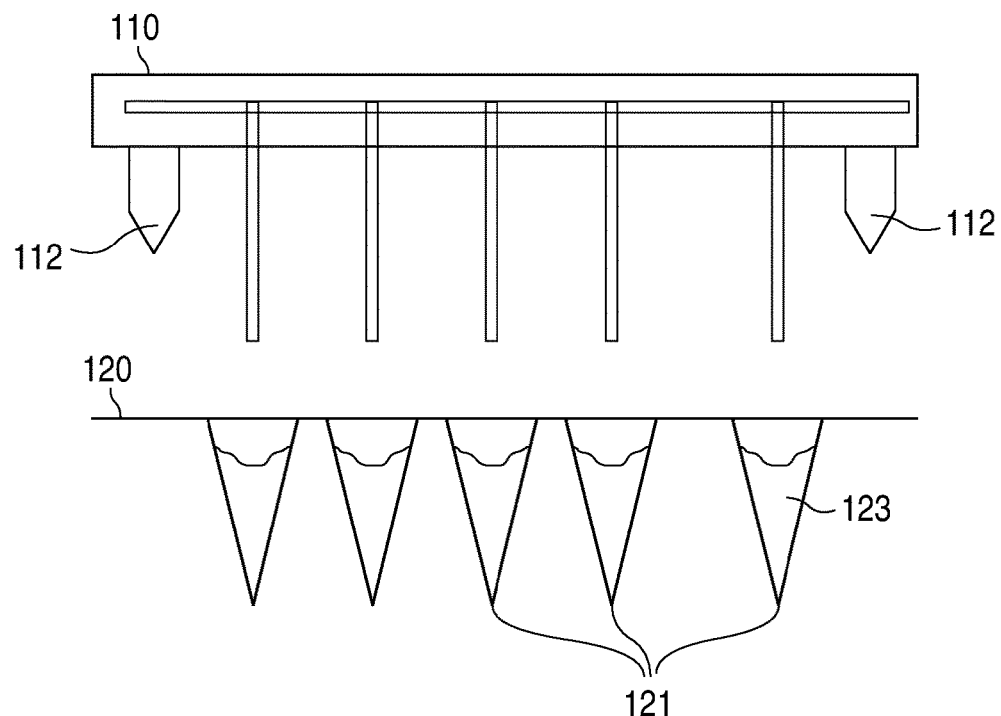
FIG. 3 is a schematic illustration of a reagent tube assembly prior to being affixed to a reaction card in accordance with the present invention.

As illustrated in FIGS. 1 and 3, reaction card 110 includes a plurality of tubular members 111 extending out from the card. The number of tubular members may vary from one to n members, with a single tubular member being illustrated in each of FIGS. 4-6 (at 411, 511, and 611). The tubular member may be a flexible tube, a rigid tube, a capillary, a cannula, or another tubular member.

One embodiment of the reaction card, illustrated at 410 in FIG. 4, comprises a channel network (channels 441, 442, and 443), a valve 414, and a micropump 415, all of which are disposed within the card. A collection well 416 is disposed on a surface of the card, and tubular member 411 can be seen extending out from the card. A vent 413 enables valve 414 to be opened to atmosphere. In all reaction card embodiments, the valve(s) and the micropump(s) are operably connected with the channel network, and the vent(s), tubular member(s), and collection well are in fluid communication with the channel network.

The number of valves, micropumps, channels, and vents included in a reaction card may vary. For example, the reaction card illustrated at 510 in FIG. 5 includes not only a first micropump 515*a*, but also a second micropump 515*b*. Like the embodiment illustrated in FIG. 4, reaction card 510 includes a single tubular member 511, a single vent 513, and a single valve 514. The channel network of reaction card 510 includes channels 541, 542, 543, 544, and 545. Reaction card 510 also includes both a collection well 516 and a waste well 517.

The reaction card illustrated at 610 in FIG. 6 includes a single tubular member 611; two vents 613*a* and 613*b*; three valves 614*a*, 614*b*, 614*c*; and two micropumps 615*a* and 615*b*. Reaction card 610 also includes both a collection well 616 and a waste well 617. Note that in all of the reaction card embodiments, channel lengths and collection well capacity are optimized so as to reduce volumes of materials and waste.

A reaction vessel assembly is affixed to the reaction card such that a tubular member is inserted into each reaction vessel. One embodiment of a reaction vessel assembly is illustrated at 130 in FIG. 1, and individual reaction vessels can be seen in FIGS. 1 and 4-6 at 131, 431, 531, and 631, respectively. The reaction vessels are shown as conical but might also be round-bottomed or take other shapes. A reaction vessel assembly may include any number of reaction vessels, with a reaction vessel assembly being made up of a single reaction vessel or multiple vessels.

Where a reagent tube assembly is included in the system, the reagent tube assembly is also affixed to the reaction card such that a tubular member is inserted into each reaction vessel. As can be seen in FIG. 1, the reaction tube assembly and reagent tube assembly may have essentially the same shape. A reagent tube assembly, however, includes one or more reagents 123 disposed in each tube. The reagent(s) may be for performing an amplification reaction such as a polymerase chain reaction (PCR) or other amplification method, including, but not limited to, reverse-transcriptase PCR (RT-PCR), nucleic acid sequence-based amplification (NASBA), transcription-based amplification system (TAS), self-sustained sequence replication (3SR), ligation amplification reaction (LAR), Q-beta amplification, and ligase chain reaction (LCR).

Figure 2:
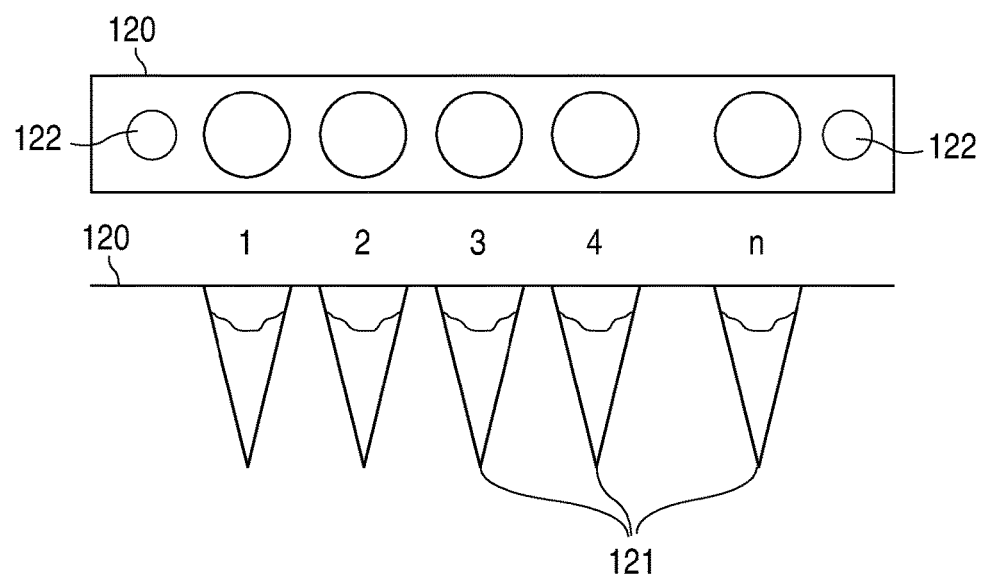
FIG. 2 is a schematic illustration of a reagent tube assembly, in accordance with the present invention, showing top and side views of the assembly.

FIG. 2 shows both a top view and a side view of a reagent tube assembly. FIG. 3 shows reagent tube assembly 120 prior to being affixed to reaction card 110. Note that, FIGS. 2 and 3 may be seen as illustrating either a reagent tube assembly or a reaction vessel assembly, with reagent(s) 122 being absent from the reaction vessel assembly. A reagent tube or reaction vessel assembly may be configured as either a linear or a two-dimensional array, a linear array being illustrated in FIGS. 1-3.

One or both of the reaction vessel assembly and the reagent tube assembly may be affixed to the reaction card using one or more mechanical locking mechanisms. One such mechanism is illustrated in FIGS. 2 and 3 at 112 and 122. Pegs 112 on reaction card 110 are inserted into openings 122 on either a reagent tube or reaction vessel assembly and are retained by friction. Pegs 112 may, of course, take other shapes and may be retained within openings 122 by means other than friction. The one or more locking mechanisms may be configured to prevent incorrect orientation of the reaction vessel or reagent tube assembly with respect to the reaction card when the assembly is affixed to the reaction card. For example, the openings may be positioned differently on each end of an assembly, with one hole positioned closer to an edge of the assembly than the other, as seen in FIG. 1.

Both the reagent tube assembly and the reaction vessel assembly may further comprise a sealing means through which a tubular member extends when the assembly is affixed to the reaction card. Sealing means are shown, for example, in FIGS. 4-6 at 432, 532, and 632, respectively. The sealing means may be pierced by a tubular member when the reagent tube assembly or the reaction vessel assembly is affixed to the reaction card, or the sealing means may include an opening through which the tubular member is inserted. A reagent tube assembly containing reagents may, for example, be sealed with an appropriate material to allow easy storage without the potential problems associated with leakage or evaporation. The seal may be thermally applied to maximize the effectiveness of the seal. Alternatively or additionally, sealing means 432, 532, and 632 may be, for example, an O-ring and may be used as a sealing member in attaching the reagent tube or reaction vessel to the reaction card. A micropump contained within the reaction card can be used to extract the reagent(s) from a reagent tube through the tubular member inserted into the tube.

A system for processing samples according to the present invention may further comprise an analysis device, a detector in sensory communication with the analysis device, and a processor operably coupled to the reaction card and the analysis device. As used herein, the phrase "in sensory communication" refers to positioning of a detector such that it is operably connected to the analysis device, i.e., capable of receiving a detectable signal from the contents of the device. In the case of optical signals, this requires only that the detector be positioned to receive the optical signal. The analysis device may be configured to perform an electrophoretic separation. One such analysis device is, for example, a PerkinElmer LabChip GX® instrument. The processor may be, for example, a computer system either external to or incorporated into the analysis device. The computer system may additionally be used to display and store information gathered as a result of the operation of the analysis device.

The above systems can be used to process samples using PCR protocols for real-time PCR and/or end-point PCR (also commonly known as rtPCR or qPCR [quantitative PCR]). Thus, another aspect of the present invention is a method for processing samples. In the method, a reaction card is provided, the reaction card comprising a channel network, a valve, and a micropump, all of which are disposed within the card. The reaction card further comprises a collection well disposed on a surface of the card and a first tubular member extending out from the card. A reaction vessel is provided and affixed to the reaction card such that the tubular member is inserted into the reaction vessel. One or more amplification reaction reagents and a sample are delivered into the reaction vessel, and an amplification reaction is initiated within the reaction vessel, resulting in an amplification product being disposed within the reaction vessel. The valve is opened to atmosphere, and the micropump is activated to pump a first aliquot of reaction product from the reaction vessel into the tubular member, through the channel network, and into the collection well.

Preferably the amplification reaction is not stopped during the steps of opening the valve to atmosphere and pumping the first aliquot of reaction product from the reaction vessel to the collection well.

The method may additionally include aspirating some or all of the first aliquot of reaction product from the collection well into an analysis device and analyzing the first aliquot of reaction product, the analysis preferably carried out using an electrophoretic separation method. Analyzing the first aliquot of reaction product may comprise quantitating nucleic acids within the first aliquot of reaction product.

The provided reaction card may further comprise a waste well and a second micropump, and the method may further comprise pumping any of the first aliquot of reaction product not aspirated into the analysis device out of the collection well and into the waste well using the second micropump.

The method may also include disposing a rinse solution in the collection well and pumping the rinse solution out of the collection well and into the waste well using the second micropump.

More than one aliquot of reaction product may be removed from the reaction vessel of the reaction card for analysis. Therefore, the method described above may further comprise closing the previously opened valve and deactivating the first and second micropumps prior to performing a second analysis. The method then comprises reopening the valve to atmosphere, reactivating the first micropump to pump a second aliquot of reaction product from the reaction vessel into the tubular member, through the channel network, and into the collection well; aspirating some or all of the second aliquot of reaction product from the collection well into the analysis device; and analyzing the second aliquot of reaction product. The amplification reaction is preferably not stopped until after the second aliquot of reaction product has been pumped into the collection well.

The method may be repeated multiple times to obtain and analyze as many aliquots of reaction product as are desired or as are contained within the reaction vessel. Preferably the amplification reaction is not stopped until all aliquots have been sampled. By analyzing multiple aliquots during the amplification reaction, real-time, quantitative PCR may be carried out.

When performing a PCR amplification reaction, a DNA sample is denatured at a relatively high temperature. The DNA is then annealed at a low temperature, and extension occurs at an intermediate temperature. Therefore, the steps of opening the valve and activating the micropump to pump an aliquot of reaction product into the collection well are preferably carried out during an annealing stage because pressure within the reaction vessel is reduced at the low annealing temperature. Opening the valve under reduced pressure diminishes the possibility of pushing reaction product out of the vent associated with the valve when opening the valve to atmospheric pressure. Reaction product located in the collection well may be analyzed throughout the remainder of the PCR cycle until the next sample is required. The annealing stage may be extended if desired to allow more time for withdrawal and analysis of the aliquot.

It is anticipated that there may not be a need to analyze a reaction product aliquot during each and every cycle. It may be adequate, for example, to analyze an aliquot after every second, third, or more cycles. This allows more time for analyzing each aliquot. It may, however, be necessary with low- or single-copy samples to perform a minimum number of cycles before taking a first aliquot from the reaction vessel in order to ensure that amplicons of the target material remain in the reaction vessel after the aliquot is removed.

Example 1

The method of processing samples is carried out using the system of FIG. 4 as follows. Reaction vessel 431 is affixed to reaction card 410 such that tubular member 411 is inserted into the reaction vessel. One or more amplification reaction reagents and a sample are delivered into reaction vessel 431, and an amplification reaction is initiated within the vessel. Valve 414 is opened to vent to atmospheric pressure, and micropump 415 is used to pump an aliquot of reaction product from reaction vessel 431 into tubular member 411 and through channels 442 and 443 into collection well 416. Some or all of the aliquot of reaction product may then be aspirated into an instrument such as a PerkinElmer LabChip® GX instrument and analyzed by the instrument. The reaction product may be analyzed by electrophoresis or another analysis method.

Micropump 415 is reversed to return any unused reaction product from collection well 416 into reaction vessel 431. Valve 414 is then closed to seal reaction vessel 431. The method may be repeated to analyze multiple aliquots of reaction product.

One limitation of the device illustrated in FIG. 4 is the potential for cross-contamination unless a dedicated aspiration device is used to analyze each collection well when an array of collection wells is present on a reaction card. Therefore, the system of FIG. 4 may be best suited to performing end-point PCR.

Example 2

The method of processing samples is carried out using the system of FIG. 5 as follows. Reaction vessel 531 is affixed to reaction card 510 such that tubular member 511 is inserted into the reaction vessel. One or more amplification reaction reagents and a sample are delivered into reaction vessel 531, and an amplification reaction is initiated within the vessel. Valve 514 is opened to vent to atmospheric pressure, and micropump 515a is used to pump an aliquot of reaction product from reaction vessel 531 into tubular member 511 and through channels 542 and 543 into collection well 516. Because channel 543 is connected to collection well 516 near the top of the well, the well can be partially filled to below the level of channel 543, and micropump 515a can be reversed to return reaction product remaining within channels 542 and 543 to reaction vessel 530. Valve 514 is then closed, and some or all of the reaction product within collection well 516 is aspirated from the well into an instrument such as a PerkinElmer LabChip® GX instrument and analyzed by the instrument. The reaction product may be analyzed by electrophoresis or another analysis method.

Collection well 516 is then emptied to waste well 517 using micropump 515b. Alternatively, if carryover is not a concern, all unused reaction product may be returned to reaction vessel 530 rather than being pumped to waste well 517.

With all valves closed and all micropumps stopped, a rinse solution may be delivered into collection well 516 to prepare the well for the next aliquot of reaction product. The rinse solution within collection well 516 is then pumped to waste well 517 using micropump 515b. The method is repeated to analyze multiple aliquots. The system of FIG. 5 may be used in performing either end-point PCR or real-time, quantitative PCR.

Example 3

The method of processing samples is carried out using the system of FIG. 6 as follows. Reaction vessel 631 is affixed to reaction card 610 such that tubular member 611 is inserted into the reaction vessel. One or more amplification reaction reagents and a sample are delivered into reaction vessel 631, and an amplification reaction is initiated within the vessel. Valves 614a and 614b are opened to vent to atmospheric pressure, and micropump 615a is used to pump an aliquot of reaction product from reaction vessel 631 into tubular member 611 and into channels 642, 643, and 644. It is not necessary to completely fill channel 644 because only a small amount of reaction product is needed for analysis.

Micropump 615a is stopped, and valves 614a and 614b are closed. Valve 614c is then opened and micropump 615a is used to pump the reaction product within channels 642, 643, and 644 through channels 645 and 646 into collection well 616. Pumping stops before all of the reaction product has been pushed from channel 646 so that air is not pushed into the collection well where it might create bubbles.

Valve 614c is then closed and micropump 615a deactivated, and some or all of the reaction product within collection well 616 is aspirated from the well into an instrument such as a PerkinElmer LabChip® GX instrument and analyzed by the instrument. The reaction product may be analyzed by electrophoresis or another analysis method.

Valve 614c remains closed while valves 614a and 614b are opened, and micropump 615a is used to return reaction product remaining in channels 642 and 643 to reaction vessel 631. All valves are then closed, and micropump 615a is stopped. Air in the channels should not be pushed into the reaction vessel.

With all valves closed and micropump 615a stopped, collection well 616 is then emptied to waste well 617 using micropump 615b. Any reaction product remaining in channel 646 is also emptied to waste by opening valve 614c and activating one or both of micropumps 615a and 615b.

With all valves closed and all micropumps stopped, a rinse solution may then be delivered into collection well 616 to prepare the well for the next aliquot of reaction product. The rinse solution within collection well 616 is then pumped to waste well 617 using micropump 615b. The method is repeated to analyze multiple aliquots. The system of FIG. 6 may be used in performing either end-point PCR or real-time, quantitative PCR.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

The invention claimed is:

1. A method of processing samples, the method comprising:
   providing:
   a reaction card, the reaction card comprising a channel network, a valve, and a first micro-pump, all of which are disposed within the card, the valve and the first micro-pump being operably connected with the channel network;
   a collection well disposed on a surface of the card; and
   a tubular member extending out from the card, the collection well and the tubular member being in fluid communication with the channel network;
   providing a reaction vessel;
   affixing the reaction vessel to the reaction card by a mechanical locking mechanism, such that the tubular member is inserted into the reaction vessel;

receiving, by the reaction vessel, one or more amplification reaction reagents and a sample;

amplifying the amplification reagents and the sample within the reaction vessel to create a reaction product;

opening the valve to atmosphere; and activating the first micro-pump to pump a first aliquot of the reaction product from the reaction vessel into the tubular member, through the channel network, and into the collection well.

2. The method of claim 1 further comprising:

aspirating the first aliquot of reaction product having been pumped into the collection well, into an analysis device; and analyzing, by the analysis device, the aspirated first aliquot of reaction product, the analysis device being in sensory communication with a detector and operably coupled to a processor.

3. The method of claim 2 wherein analyzing the first aliquot of reaction product comprises quantitating nucleic acids within the first aliquot of reaction product.

4. The method of claim 3 wherein the first aliquot of reaction product is analyzed using an electrophoretic separation method.

5. The method of claim 2 wherein the reaction card further comprises a waste well and a second micropump, the method further comprising:

pumping any of a first aliquot of reaction product not aspirated into the analysis device out of the collection well and into the waste well using the second micropump, the collection well being in fluid communication with the waste well.

6. The method of claim 5 further comprising:

disposing a rinse solution in the collection well; and pumping the rinse solution out of the collection well and into the waste well using the second micropump.

7. The method of claim 1 wherein the amplification reaction is not stopped until the first aliquot of reaction product has been pumped into the collection well.

8. The method of claim 1 wherein the opening and activating steps are carried out during a polymerase chain reaction annealing stage.

9. The method of claim 6 further comprising:

closing the valve;

deactivating the first and second micropumps;

reopening the valve to atmosphere;

reactivating the first micropump to pump a second aliquot of reaction product from the reaction vessel into the tubular member, through the channel network, and into the collection well;

aspirating the second aliquot of reaction product from the collection well into the analysis device; and analyzing, by the analysis device, the second aliquot of reaction product, the analysis device being in sensory communication with a detector and operably coupled to a processor.

10. The method of claim 9 wherein the amplification reaction is not stopped until after the second aliquot of reaction product has been pumped into the collection well.

11. The method of claim 9 wherein analyzing the second aliquot of reaction product comprises quantitating nucleic acids within the second aliquot of reaction product.

12. The method of claim 9 wherein the second aliquot of reaction product is analyzed using an electrophoretic separation method.

* * * * *